US00PP25304P3

(12) United States Plant Patent
Kardos

(10) Patent No.: US PP25,304 P3
(45) Date of Patent: Feb. 24, 2015

(54) ***DISTYLIUM* PLANT NAMED 'PIIDIST-III'**

(50) Latin Name: ***Distylium* sp. hybrid**
Varietal Denomination: PIIDIST-III

(71) Applicant: Joshua H. Kardos, Watkinsville, GA (US)

(72) Inventor: Joshua H. Kardos, Watkinsville, GA (US)

(73) Assignee: Plant Introductions, Inc., Watkinsville, GA (US)

( * ) Notice: Subject to any disclaimer, the term of this patent is extended or adjusted under 35 U.S.C. 154(b) by 127 days.

(21) Appl. No.: 13/815,683

(22) Filed: Mar. 14, 2013

(65) Prior Publication Data
US 2014/0283244 P1 Sep. 18, 2014

(51) Int. Cl.
*A01H 5/00* (2006.01)

(52) U.S. Cl.
USPC ..... Plt./226

(58) Field of Classification Search
USPC ..... Plt./226
See application file for complete search history.

*Primary Examiner* — Annette Para
(74) *Attorney, Agent, or Firm* — Lathrop & Gage LLP

(57) ABSTRACT

A new and distinct cultivar of *Distylium* plant named 'PIIDIST-III', characterized by its compact, rounded to spreading growth habit, bronze-purple new growth, dark bluish green mature foliage, and reddish maroon flowers.

3 Drawing Sheets

Genus and species of plant claimed: *Distylium* sp. hybrid. Variety denomination: 'PIIDIST-III'.

BACKGROUND OF THE INVENTION

The present invention relates to a new and distinct cultivar of *Distylium* plant, botanically known as *Distylium* sp. hybrid, a member of the Hamamelidaceae, and hereinafter referred to by the cultivar name 'PIIDIST-III'. 'PIIDIST-III' is grown primarily as an ornamental for landscape use and for use as a potted plant.

'PIIDIST-III' originated in 2008 as an open-pollinated seedling from bulk seed collected from several unnamed and unpatented selections of *Distylium* sp. hybrids as part of a breeding program in Watkinsville, Ga. Due to the bulk seed collection, the exact parents are unknown. 'PIIDIST-III' originated and was selected by the inventor in a cultivated environment in Watkinsville, Ga. from the progeny of this open-pollination by continued evaluation for growth habit and foliage characteristics.

Asexual reproduction of 'PIIDIST-III' by stem cuttings in Watkinsville, Ga. since 2010 has shown that all the unique features of 'PIIDIST-III', as herein described, are stable and reproduced true-to-type through successive generations of such asexual propagation.

SUMMARY OF THE INVENTION

Plants of the new cultivar 'PIIDIST-III' have not been observed under all possible environmental conditions. The phenotype may vary somewhat with changes in light, temperature, soil and rainfall without, however, any variance in genotype.

The following traits have been repeatedly observed and are determined to be unique characteristics of 'PIIDIST-III'. These characteristics in combination distinguish 'PIIDIST-III' as a new and distinct cultivar: 1. Compact, rounded to spreading growth habit; 2. Bronze-purple new growth; 3. Dark bluish green mature foliage; and 4. Reddish maroon flowers.

Plants of the new *Distylium* 'PIIDIST-III' can be compared to plants of the cultivar 'PIIDIST-II' (U.S. Plant Pat. No. 24,409), but differ in growth habit and foliage color. 'PIIDIST-III' has a compact, rounded to spreading growth habit and bronze-purple new growth that matures to bluish green, whereas 'PIIDIST-III' has a compact, spreading growth habit and maroon-purple new growth that matures to darker blue-green.

BRIEF DESCRIPTION OF THE DRAWINGS

The accompanying color photographs illustrate the flower and foliage characteristics and the overall appearance of 'PIIDIST-III', showing the colors as true as it is reasonably possible to obtain in color reproductions of this type. Colors in the photographs may differ slightly from the color values cited in the detailed botanical description which accurately describe the colors of 'PIIDIST-III'.

DETAILED DESCRIPTION

Figure 1:
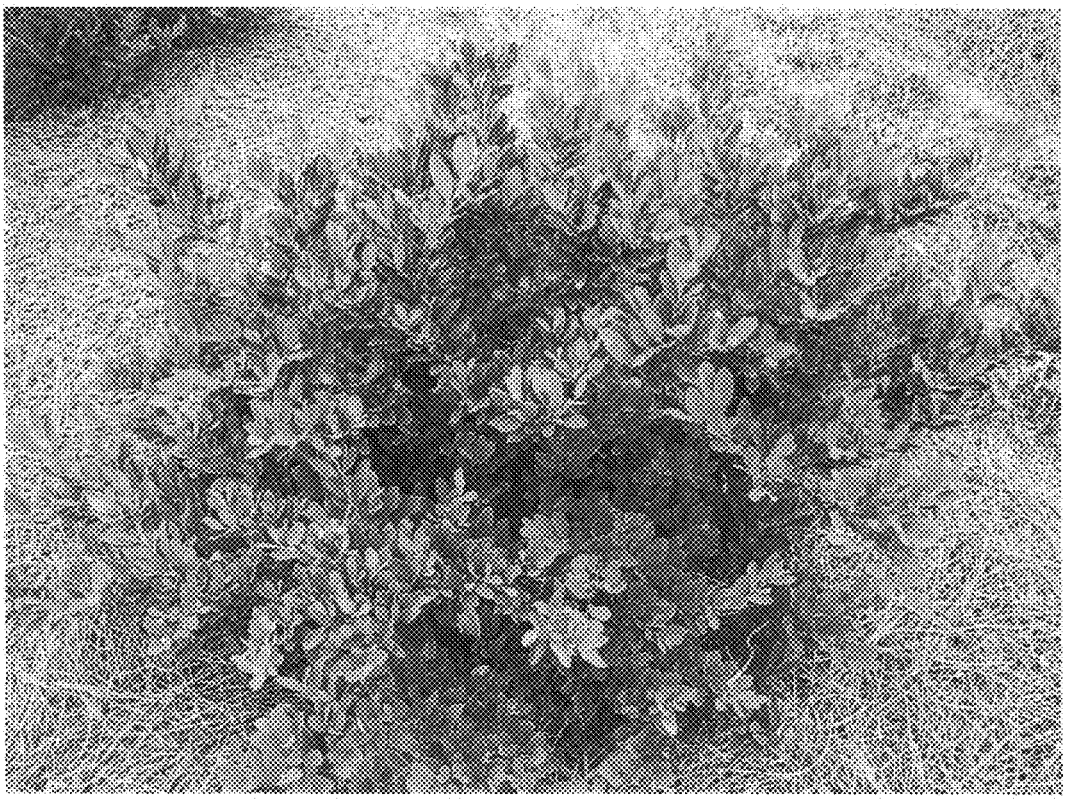
FIG. 1 illustrates the overall appearance and growth habit of a mature plant of 'PIIDIST-III' planted in the ground.
Figure 2:
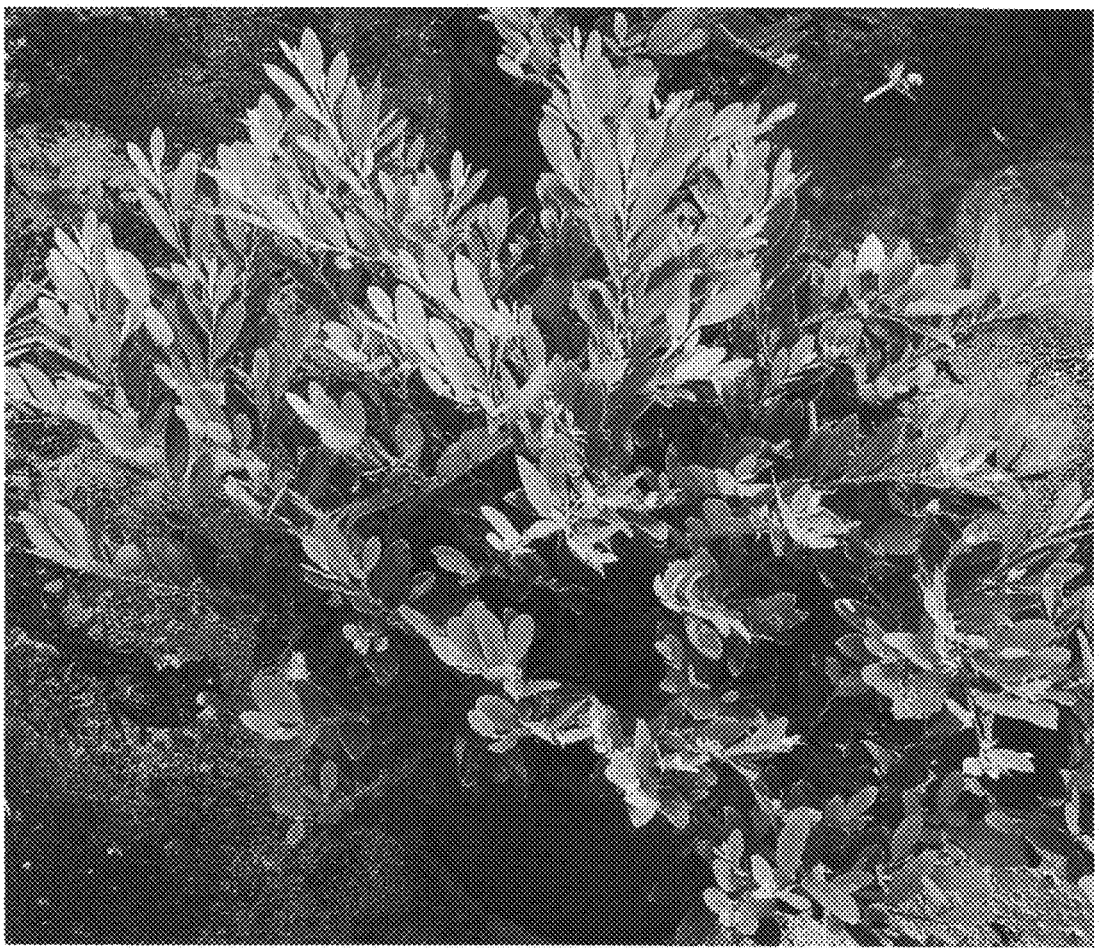
FIG. 2 illustrates new growth and mature foliage of a plant of 'PIIDIST-III' growing in a container.
Figure 3:
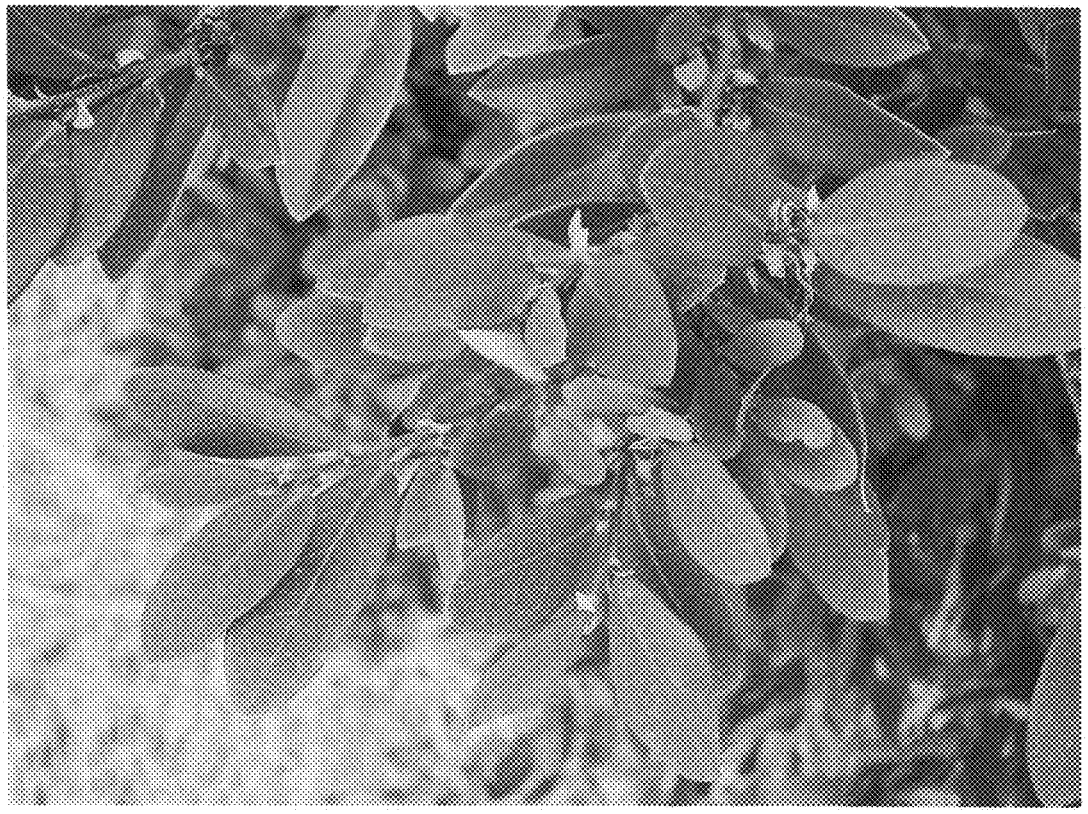
FIG. 3 illustrates a close-up view of the new growth of 'PIIDIST-III'.

In the following description, color references are made to The Royal Horticultural Society Colour Chart, 2007 Edition, except where general terms of ordinary dictionary significance are used. Plants used for the description were approximately 2-years-old and were grown in 11.8 L containers under outdoor conditions in Watkinsville, Ga.

Botanical classification: *Distylium* sp. hybrid, cultivar 'PIIDIST-III'. Parentage: *Distylium* sp. hybrid (unnamed and unpatented). Propagation: stem cuttings. Time to initiate roots in summer: about 28 days at 32° C.

Plant description: Broadleaf evergreen flowering shrub; multi-stemmed; compact, rounded to spreading growth habit. Freely branching; removal of the terminal bud enhances lateral branch development.

*Root description*.—Medium, well-branched.

*Plant size*.—The original plant, now about four and a half-years-old in the ground, is about 91 cm high from the soil level to the top of the foliage and about 147 cm wide.

*First year stems*.—Having a diameter of about 2 mm. Shape: round. Fine pubescence. Few small lenticels about 1 mm in diameter and N199B in color.

*First year stem color*.—146B.

*Second year and older stems*.—Have a diameter of about 4 mm or more. Shape: round.

*Second year and older stem color*.—199B.

*Stem strength*.—Flexible when young, less so with maturity.

*Internode length*.—About 1.3 cm.

*Trunk diameter*.—About 3.1 cm at the soil line.

*Color*.—199A.

*Bark*.—Does not exfoliate, covered with many lenticels about 1 mm in diameter and N199B in color.

Vegetative buds:

*Arrangement*.—Alternate.

*Shape*.—Ovoid with fused, pubescent bud scales.

*Size*.—About 3 mm in length and about 1.5 mm in width.

*Color*.—164B.

Foliage:

*Arrangement*.—Alternate, simple.

*Length*.—About 6.1 cm.

*Width*.—About 2.3 cm.

*Shape*.—Elliptical.

*Apex*.—Acute.

*Base*.—Cuneate.

*Margin*.—Entire and undulating, occasionally with up to 3 teeth toward apex.

*Texture* (*upper and lower surfaces*).—Thick, leathery, also glaucous on upper surface.

*Venation pattern*.—Pinnate.

*Venation color* (*upper and lower surfaces*).—Color is 147B.

*Color of emerging foliage* (*upper surface*).—A combination of 181C and N77D.

*Color of emerging foliage* (*lower surface*).—193B.

*Color of mature foliage* (*upper surface*).—N189A.

*Color of mature foliage* (*lower surface*).—138B.

*Petiole length*.—About 3 mm.

*Petiole diameter*.—About 1 mm.

*Fine pubescence*.—199B in color.

*Petiole color* (*upper and lower surfaces*).—146B.

Flowers:

*Flower type and habit*.—Apetalous flowers with a pubescent, 5-parted calyx are borne on short racemes from the leaf axils.

*Natural flowering season*.—Late winter, approximately January to February in Watkinsville, Ga. Individual flowers are showy for approximately 1 week and are self-cleaning.

*Flower size*.—About 1 cm in diameter and about 1 cm in height.

*Pedicels*.—About 1.9 mm in length.

*Peduncles*.—About 1.1 cm in length.

*Color*.—Pedicels and peduncles 146C in color with pubescence 165A in color.

Stamens:

*Quantity/arrangement*.—7 to 10 per flower.

*Filament*.—About 3 mm in length, less than 1 mm in width, and 146D in color.

*Anthers*.—About 2 mm in length, about 1 mm in width, and 185A in color.

*Pollen*.—Produced in moderate quantities and is 158D in color.

Pistils:

*Position*.—Superior.

*Size*.—About 1.1 cm in length and about 2 mm in width.

*Color*.—146B.

*Stigma*.—2 per pistil, about 6 mm in length, 178B in color.

*Style*.—2 per flower, about 3 mm in length, and 146B in color.

*Ovary*.—Two per flower, about 2 mm in diameter, about 2 mm in height, and 146B in color.

Fruit: None observed to date.

Disease/pest resistance: Plants of the new *Distylium* grown in the nursery and garden have not been noted to be susceptible to pathogens or pests.

I claim:

1. A new and distinct *Distylium* plant named 'PIIDIST-III', as illustrated and described herein.

* * * * *